United States Patent [19]

Rees

[11] 4,395,492
[45] Jul. 26, 1983

[54] PERFUSION CHAMBER

[75] Inventor: Douglas Rees, Wellington, New Zealand

[73] Assignee: Res-Del Group Ltd., Wellington, New Zealand

[21] Appl. No.: 270,139

[22] Filed: Jun. 3, 1981

[51] Int. Cl.³ .......................... A01N 1/02; E03C 1/24
[52] U.S. Cl. ...................................... 435/283; 4/201; 4/202; 4/538
[58] Field of Search ................... 435/283; 4/194, 201, 4/202, 538

[56] References Cited

U.S. PATENT DOCUMENTS

| | | | |
|---|---|---|---|
| 3,545,221 | 12/1970 | Swenson et al. | 435/283 X |
| 3,639,084 | 2/1972 | Goldhaber | 435/283 X |
| 3,738,914 | 6/1973 | Thorne et al. | 435/283 |
| 3,772,153 | 11/1973 | DeRoissart | 435/283 |
| 3,777,507 | 12/1973 | Burton et al. | 435/283 X |
| 3,914,954 | 10/1975 | Doerig | 435/283 X |
| 3,935,065 | 1/1976 | Doerig | 435/283 X |
| 3,995,444 | 12/1976 | Clark et al. | 435/283 X |

FOREIGN PATENT DOCUMENTS 124384 3/1919 United Kingdom .

OTHER PUBLICATIONS

B. J. O'Brien, "Effect of Inorganic Phosphate Ions . . . Perfused Rat Heart Preparations", Victoria University, Wellington, N.Z., 1981.
Brian Robinson, "A Pharmacological Investigation . . . Detrusor Musculature of the Rat", Victoria University, Wellington, N.Z., 1980.
Experimental Neurology, v. 40, pp. 183–188, 1973.
Brain Research, v. 85, p. 424, 1975.
J. Physiol., v. 275, p. 536, 1978.
J. Neuroscience, Melbourne, v. 1, p. 324, 1979.
Brain Research, v. 152, p. 592, 1978.
J. Physiol., v. 249, p. 563, 1975.
J. Exp. Biology, v. 52, p. 259, 1970.
J. Physiol., v. 199, 1968.
J. Exp. Biology, v. 69, 1973.
Brain Research, v. 105, p. 478, 1976.
Ealing Catalog, pp. 69, 75, F10.

Primary Examiner—Robert J. Warden
Attorney, Agent, or Firm—Pasquale A. Razzano; Harold L. Stults

[57] ABSTRACT

A bath for use in the study of in vitro maintained human or animal tissue, comprises a body having a bath cavity provided with at least one fluid inlet port 2, and a spillway 6 formed in the wall of the bath acting as a fluid outlet. The upper edge 5 of the spillway determines the fluid level in the bath, and a pivotally mounted choke 7 co-acting with the surface of the spillway regulates the flow of fluid from the bath. The bath is also provided with at least one gas inlet port 18 adapted to form a layer of gas over the surface of the fluid so as to insulate the fluid from the surrounding air.

10 Claims, 4 Drawing Figures

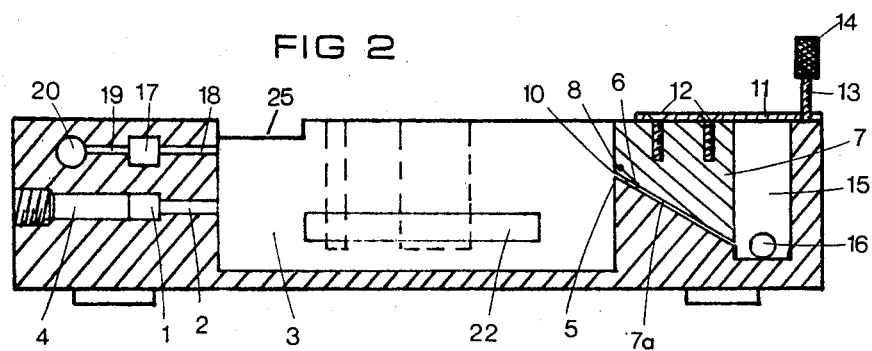
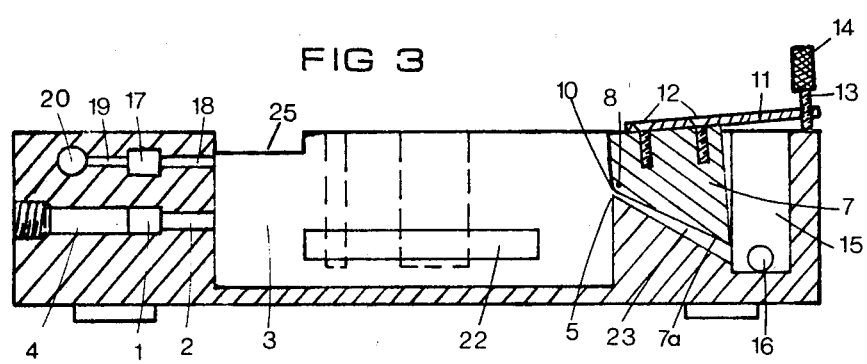
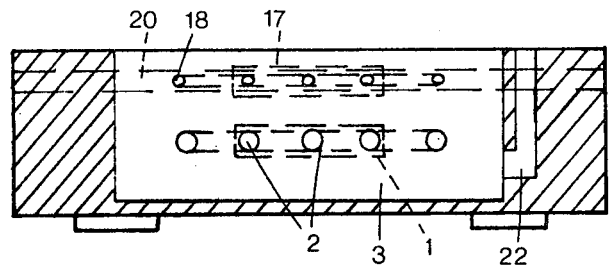

PERFUSION CHAMBER

This invention relates to an improved perfusion bath for studies of in vitro maintained human and animal tissue. Such studies are generally undertaken in a bath made wholly or partly of glass or similar transparent material. During such study it is necessary that the tissue be immersed in a physiologically balanced solution or other suitable liquid which is subjected to a controlled flow through the bath to allow the disposal of debris and other unwanted matter from the bath. It is also necessary that the surface of the liquid be shielded from ambient air in order that the gas content of the liquid can be maintained within predetermined levels.

Previously known forms of such baths utilise a fluid drain on an over-flow principle so that the surface of the fluids would be continually drained as the fluid is being replenished. One of the difficulties experienced with known baths is that the drain hole or holes tend to block as a result of surface tension, and thus an undesirable fluctuation in the level of the fluid in the bath occurs.

It is therefore an object of this invention to provide an improved bath in which the level of the fluid within the bath can be maintained substantially constant throughout substantial variations in the rate of fluid flow into the bath.

It is another object of the invention to provide a bath having a higher rate of fluid flow through the bath, than previously known forms of perfusion baths.

It is a further object of the invention to provide a perfusion bath which is less susceptible to vibration of the suspended tissue preparation, than previously known forms of perfusion baths.

Accordingly, one form of the invention may be said to comprise a bath for use in the study of in vitro maintained human or animal tissue, comprising a body having a bath cavity, means to allow fluid entry into the said bath cavity and means to allow fluid exit from the said bath cavity, wherein the means to allow fluid exit from the said bath cavity comprises a spillway formed into a wall of the bath, said spillway having an upper edge adapted to determine the maximum level of fluid in the said bath cavity and said spillway being provided with means to regulate the fluid flow from the bath.

In a preferred form of the invention the bath is formed from a suitable plastics material so as to be essentially in the form of an open topped box-like structure. One or more walls are provided with a fluid entry which is preferably at least one port which communicates with the interior of the bath adjacent to floor thereof, with the port or ports being connected by suitable ducting or the like to valving arrangements so that a controlled flow of fluid can enter into the bath. One wall is provided with a spillway, the upper surface of which slopes downwardly from the bath, with the entry to the spillway determining the height of the fluid within the bath. Fluid which spills over the spillway will pass into a suitable drain formed integrally in the wall of the bath for subsequent disposal.

Means are provided for controlling the flow of fluid over the spillway, such means being a choke preferably in the form of an elongated wedge which may also be formed of a plastics material and which is shaped to complement the shape of the spillway. The choke will co-act with the spillway so as to regulate the amount of fluid and extraneous matter which passes over the spillway into the said drain. Preferably the spillway extends the full width of the bath and thus provides a relatively long path for the discharge of the excess fluid and other material from the bath. Means are provided to assist the ready adjustment of the choke in relation to the spillway so that the correct rate of discharge can be arranged to co-relate with the in-flow of liquid into the bath.

The bath also includes at least one gas outlet port formed in its wall or walls. These gas outlet port or ports are connected by means of a manifold to a gas inlet, so that gas can be discharged through the port or ports to flow closely over the surface of the liquid in the bath. For this purpose the gas outlet port or ports are aligned in the said walls and are spaced apart and of a diameter to allow the desired flow of gas over the surface of the liquid. The gas outlet port or ports are positioned slightly above the level of the top edge of the said spillway. The gas to be utilised may be a mixture of various gases as is known in the art and its purpose is to provide the required protection for the contents of the bath by insulating the surface of the fluid from ambient air. One preferred form of gas may for instance be a mixture of 95% oxygen and 5% carbon dioxide.

A preferred embodiment of the invention will now be described with the aid of the accompanying diagrams wherein:

FIG. 2 is a cross sectional view of FIG. 1 along line II—II showing the bath in the least flow mode of operation, and, FIG. 3 is a cross sectional view of FIG. 1 along a line II—II showing the bath in a high flow mode of operation.

FIG. 4 is a cross sectional view of FIG. 1 along a line III—III showing the gas and fluid inlet ports in the opposite end wall of the bath.

Figure 1:
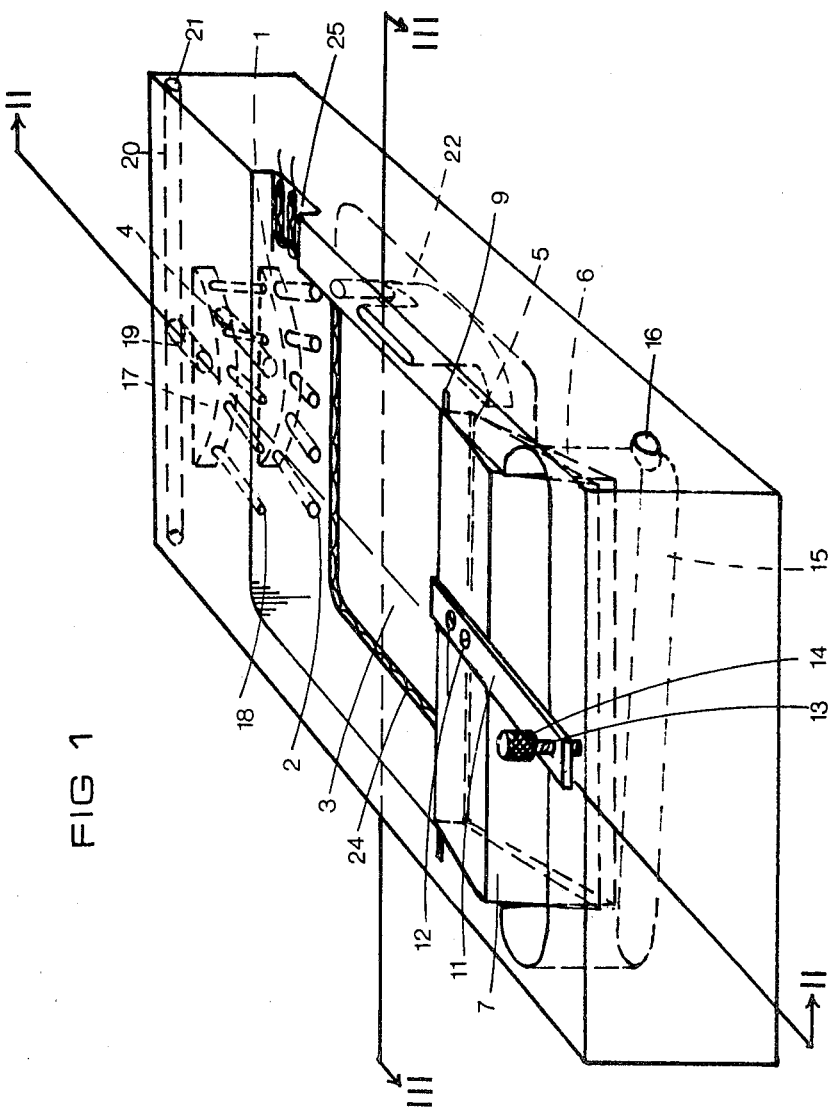
FIG. 1 is a view of a preferred embodiment of the perfusion bath.

With reference to the drawings, the bath is formed preferably from a plastics material such as that known under the trade mark PERSPEX, and has a fluid inlet manifold 1 which is provided with a plurality of fluid inlet ports 2 which communicate the fluid inlet manifold 1 with the bath cavity 3. These ports are evenly spaced in a horizontal row in one wall of the bath cavity 3. A bore 4, in the wall of the bath, communicates the fluid inlet manifold 1 with the outside, and at its outer end the bore may be provided with means to enable a fluid supply to be connected to the bath, typically, by having its outer end threaded. Although it is envisaged within the invention, that there may be provided only one fluid inlet port 2, in the preferred embodiment, there are provided several inlet ports which are spaced apart along a wall or walls of the bath, so that the least disturbance is caused to the suspended tissue preparation contained in the bath, while still achieving a high inflow of fresh fluid through the fluid inlet ports 2.

One wall of the bath is provided with a cutout section, so as to provide a substantially horizontal edge 5, and the upper surface of this wall within the cutout section, is formed into a sloping surface which slopes downwardly from the horizontal edge so as to form a spillway 6. Cooperating with the sloping spillway 6 is a choke 7, which may be of any shape, but in the preferred embodiment is formed into an elongated wedge. The choke 7 is of the same length along its longitudinal axis, as the length of the horizontal edge 5, and its lower surface 7a is formed so as to be complementary with the sloping surface of the spillway 6. In the preferred embodiment, these two surfaces are machined so as to be substantially plane and substantially smooth.

The choke 7 is mounted and pivoted about a longitudinal axis through the body of the choke 7, the axis being parallel with the spillway edge 5, and the choke is mounted in the preferred embodiment, by way of circular cross section pins 8, shown end—on in FIGS. 2 and 3 whose central axis is the same as the longitudinal axis about which the choke 7 is pivoted. The pins 8 engage within slots 9 which are formed in the body of the bath.

The nose 10 of the choke 7 is formed so as to be of a semi-circular shape, having a radius transverse to the longitudinal axis along which the pins 8 are mounted, and having as its centre of rotation, any point on the said longitudinal axis.

Furthermore the positioning and depth of the mounting slots 9 is such that the distance between the spillway edge 5 and the choke nose 10 is the same at all points along the spillway edge 5, and thus, the positioning requirements of the pins 8 and slots 9 as hereinbefore described, in conjunction with the nose 10, will ensure that the gap between the two said edges is constant, when the choke is rotated about its pivoting mountings, through an angle of anything up to typically 30° but optimally being 5°–15°. This gap will typically be, in the preferred embodiment, 1 mm.

Means to adjust the position of the choke 7 about the longitudinal axis passing through the centre of its mounting pins is provided, and in the preferred embodiment consists of a plate 11 suitably secured to the upper surface of the choke 7 by way of countersunk screws 12 or similar means, and being provided at its outermost end, with a threaded hole, through which passes a threaded pin 13 having an adjusting knob 14, the lower end of the threaded pin 13 bearing directly onto the body of the bath. When the threaded pin 13 is screwed in the direction of its threads the choke is rotated about its mountings, in a direction away from the body of the bath. Conversely when the threaded pin 13 is screwed in opposite direction to its threads, the choke will rotate in a direction towards the body of the bath.

Associated with the said adjusting means, is a stop means, which may be of suitable arrangement but in the preferred embodiment is formed by the abutment of the lower surface of the plate 11 with the body of the bath. The plate 11 is mounted onto the choke 7 is such that when the threaded pin 13 is screwed to its outermost position, and the lower surface of the plate 11 is in abutting relationship with the body of the bath, the distance between the lower surface 7a of the choke and the sloping surface of the spillway 6 is substantially equal at all points to the distance between the spillway edge 5 and the choke nose 10, (see FIG. 2). As described hereinbefore when the choke 7 is rotated about its mounting by an inward screwing of the threaded pin 13, the distance between the spillway edge 5 and the choke nose 10 will remain constant, while the distance between the sloping surface of the spillway 6, and the lower surface 7a of the choke will be increased.

With reference to the preferred embodiment hereinbefore described, it will be seen that fluid entering the bath cavity via the fluid inlet ports 2, will cause the bath to fill until the fluid contained inside the bath cavity has reached the level of the spillway edge 5. Any further fluid entering the bath cavity will cause a displacement of fluid already present in the bath cavity over the spillway edge 5, and fluid so displaced will proceed down the sloping gap 23 formed between the choke lower surface 7a and the spillway 6 and any further fluid present at the spillway edge will be drawn through the said gap 23 by a siphon effect. Furthermore, if the adjusting means is utilised to rotate the choke 7 about its mountings as hereinbefore described, the increasing gap 23 (see FIG. 3) between the spillway sloping surface, and the choke lower surface 7a will cause fluid present at the spillway edge 5 to be drawn down the spillway at a faster rate, as a result of a Bernoulli effect. Fluid so displaced will fall down the spillway and into the sump 15, the bottom surface of said sump is being sloped so as to cause any fluid present in the sump to drain out through the drain hole 16.

Inclusive to the preferred embodiment is a gas inlet manifold 17, which communicates with the bath cavity by way of gas outlet ports 18. The gas outlet ports are preferably substantially equidistally spaced apart along a wall or walls of the bath cavity and are positioned at a height slightly above the level of the spillway edge 5. A bore 20 is provided in the body of the bath in the portion adjacent to the gas inlet manifold, the said bore running transversely across the body of the bath and having one or both of its ends 21 open to the outside. The said bore 20 may be provided at one, or both of its ends 21, with means (not shown in the drawings) to enable a gas supply to be connected. A further bore 19 communicates the bore 20 with the gas inlet manifold 17, and thus gas may be supplied to the gas inlet manifold 17 by way of these bores. Gas so supplied will pass out the gas outlet ports 18, these gas outlet ports 18 are spaced apart so as to provide a layer of gas over the surface of fluid present in the bath, for the purpose hereinbefore described.

Furthermore the preferred embodiment is provided with a cutout 22 in the wall of the bath, said cutout communicating with the bath cavity at a point below the level of the spillway edge 5. This cutout may house a reference electrode, typically silver chloride and a temperature sensor (not shown in the drawings) or other electrodes as required for the studies.

Preferably the floor of the bath is coated with a transparent, non-toxic, non-absorbent resin such as Sylgard 184 to allow hold down pins to be used to position and anchor the tissue to be studied, while also serving to allow light to pass through, for visual appreciation of the suspended tissue. The bath may in addition include a thermostatically controlled electrical heating element 24 so that the fluid can be heated and then maintained at the desired temperature. A suitable recess 25 may be provided in a wall of the bath to allow connection leads for the heating element to be accessed, or to facilitate the use of a sintered gas bubbler or other like services.

I claim:

1. A bath for use in the study of in vitro maintained human or animal tissue, comprising a body having a bath cavity, means to allow fluid entry into said bath cavity, and means to allow fluid exit from said bath cavity, wherein the means to allow fluid exit from said bath cavity comprises a spillway formed into a wall of the bath, said spillway having an upper horizontal edge defining the maximum level for fluid in said bath cavity and having a spillway surface sloping downwardly from said edge, said spillway being provided with means to regulate the fluid flow from the bath cavity, said means to regulate comprising a choke having a surface cooperating with said spillway surface and adjustably separated therefrom to be maintained in a predetermined contiguous relationship with said spillway.

2. A bath for use in the study of in vitro maintained human or animal tissue, comprising a body having a bath cavity, means to allow fluid entry into said bath cavity, and means to allow fluid exit from said bath cavity, wherein the means to allow fluid exit from said bath cavity comprises a spillway formed into a wall of the bath, said spillway being formed so as to have a surface sloping downwardly from an upper edge thereof serving to define the maximum level of fluid in said bath cavity, and said spillway being provided with means to regulate the flow from the bath over the spillway, said means comprising a choke formed into an elongated wedge having a lower surface complementary to the surface of said spillway, and means for maintaining said lower surface in a predetermined contiguous relationship with the sloping surface of said spillway.

3. A bath for use in the study of in vitro maintained human or animal tissue, comprising a body having a bath cavity, means to allow fluid entry into said bath cavity, and means to allow fluid exit from said bath cavity, wherein the means to allow fluid exit from said bath cavity comprises a spillway formed into a wall of the bath, said spillway being formed so as to slope downwardly from an upper edge thereof adapted to define the maximum level of fluid in said bath cavity, and said spillway being provided with means to regulate the fluid flow from the bath cavity, said means to regulate comprising a choke in the form of an elongated wedge, adapted to have its lower surface maintained in a predetermined contiguous relationship with said spillway, wherein said choke has a nose and is pivotally mounted on a mounting therefore for rotation about an axis substantially parallel to and adjacent to the upper edge of the spillway, said mounting being arranged such that a gap of constant dimension will be maintained between said nose and said upper edge at any particular rotational position of the choke.

4. The bath as claimed in claim 3 wherein the said choke is provided with means to allow adjustment of its rotational position about the said axis.

5. The bath as claimed in any one of claims 1-4, wherein the said bath includes means to allow a gas flow over the surface of the fluid contained in the bath.

6. The bath as claimed in any one of claims 1-4, wherein the said bath includes means to create a gas flow over the surface of the fluid contained in the bath such means comprising a manifold adapted to receive a supply of gas, and at least one outlet port connected to the manifold and adapted to discharge a flow of gas over the surface of the fluid contained in the bath cavity.

7. The bath as claimed in any one of claims 1-4, wherein said means to allow fluid entry to the bath comprises a fluid manifold adapted to receive a supply of fluid, at least one port connected to the manifold, said port being formed in a wall or walls of the bath below the maximum level defined by the upper edge of the spillway.

8. The bath as claimed in any one of claims 1-4, wherein the means to allow fluid entry to the bath comprises a plurality of successive ports spaced from the next adjacent ports by substantially equal amounts.

9. The bath of any one claims 1-4 wherein the said bath is provided with a thermostatically controlled heating element.

10. The bath as claimed in any claims 1-4 wherein in the said bath is provided with a cutout section in the wall of the bath, said cutout section dimensioned to receive a reference electrode.

* * * * *